United States Patent
Deng et al.

(10) Patent No.: US 11,076,832 B2
(45) Date of Patent: *Aug. 3, 2021

(54) METHOD AND SYSTEM FOR MEDICAL IMAGING AND INFORMATION DISPLAY

(71) Applicant: KONINKLIJKE PHILIPS N.V., Eindhoven (NL)

(72) Inventors: Yinhui Deng, Shanghai (CN); Xiaomin Li, Shanghai (CN); Xiaolin Gu, Shanghai (CN); Vijay Thakur Shamdasani, Kenmore, WA (US); Ying Wu, Shanghai (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 272 days.

This patent is subject to a terminal disclaimer.

(21) Appl. No.: 16/257,524

(22) Filed: Jan. 25, 2019

(65) Prior Publication Data

US 2019/0150896 A1 May 23, 2019

Related U.S. Application Data

(63) Continuation of application No. 14/910,718, filed as application No. PCT/EP2014/067139 on Aug. 11, 2014, now Pat. No. 10,226,235.

(30) Foreign Application Priority Data

Aug. 9, 2013 (WO) ................ PCT/CN2013/081206
Nov. 22, 2013 (EP) ..................................... 13194039

(51) Int. Cl.
*A61B 8/00* (2006.01)
*A61B 8/08* (2006.01)
(Continued)

(52) U.S. Cl.
CPC ............ *A61B 8/5207* (2013.01); *A61B 8/461* (2013.01); *A61B 8/469* (2013.01); *A61B 8/5246* (2013.01);
(Continued)

(58) Field of Classification Search
CPC ..... A61B 8/5207; A61B 8/469; A61B 8/5246; A61B 8/461; A61B 8/466; A61B 8/5292;
(Continued)

(56) References Cited

U.S. PATENT DOCUMENTS 6,186,949 B1   2/2001  Hatfield
10,226,235 B2 *  3/2019  Deng ..................... G16H 30/20
(Continued)

FOREIGN PATENT DOCUMENTS

WO   2012101511 A2   8/2012

OTHER PUBLICATIONS

Ciompi et al, "Recent Advances in Biomedical Signal Processing" Chapter 15, "Reconstruction and Analysis of Intravascular Ultrasound Sequences" p. 223-243.
(Continued)

*Primary Examiner* — Joel Lamprecht

(57) ABSTRACT

The present invention provides a method and a system for medical imaging and information display. According to an aspect of the present invention, there is proposed a method of medical imaging and information display, comprising: acquiring imaging data of each point of a plurality of points in an imaging plane or imaging volume of a subject in each mode of a plurality of different imaging modes of a medical imaging apparatus; deriving, for said each point, a value by applying the imaging data of the point in said each mode and the imaging data of at least one other point of said plurality of points adjacent to the point in said each mode to a predetermined model, wherein the predetermined model is
(Continued)

selected in accordance with a clinical medical application related to the subject; constructing an image based on all the derived values; and displaying the constructed image to a user. Accordingly, the novel method of medical imaging and information display may reduce the burden of doctors, and provide them with an image with a higher definition compared to the conventional ROI method.

6 Claims, 1 Drawing Sheet

(51) Int. Cl.
| | |
|---|---|
| *G16H 50/20* | (2018.01) |
| *G16H 30/40* | (2018.01) |
| *G06F 19/00* | (2018.01) |
| *G16H 30/20* | (2018.01) |

(52) U.S. Cl.
CPC ............ *G06F 19/00* (2013.01); *G16H 30/20* (2018.01); *G16H 30/40* (2018.01); *G16H 50/20* (2018.01); *A61B 8/08* (2013.01); *A61B 8/466* (2013.01); *A61B 8/467* (2013.01); *A61B 8/483* (2013.01); *A61B 8/485* (2013.01); *A61B 8/486* (2013.01); *A61B 8/488* (2013.01); *A61B 8/5292* (2013.01)

(58) Field of Classification Search
CPC ........... A61B 8/467; A61B 8/488; A61B 8/08; A61B 8/486; A61B 8/485; A61B 8/483; G06F 19/321; G06F 19/345
See application file for complete search history.

(56) References Cited

U.S. PATENT DOCUMENTS

| | | |
|---|---|---|
| 2007/0016028 A1 | 1/2007 | Donaldson et al. |
| 2007/0016029 A1 | 1/2007 | Donaldson |
| 2008/0221446 A1 | 9/2008 | Washburn et al. |
| 2010/0121178 A1 | 5/2010 | Krishnan et al. |
| 2013/0310691 A1 | 11/2013 | Furman et al. |

OTHER PUBLICATIONS

Scheipers et al, "Ultrasonic Multifeature Tissue Characterization for Prostate Diagnostics" Ultrasound in Med. and Bio. vol. 29, No. 8, pp. 1137-1149 (2003).

* cited by examiner

METHOD AND SYSTEM FOR MEDICAL IMAGING AND INFORMATION DISPLAY

CROSS-REFERENCE TO RELATED APPLICATIONS

This application is a continuation of U.S. patent application Ser. No. 14/910,718, filed on Feb. 8, 2016, which is the U.S. National Phase Application under 35 U.S.C. § 371 of International Application No. PCT/EP2014/067139, filed on Aug. 11, 2014, which claims the benefit of both European Application No. 13194039.7, filed on Nov. 22, 2013 and PCT/CN2013/0812069, filed Aug. 9, 2013. These applications are hereby incorporated by reference herein.

FIELD OF THE INVENTION

The present invention relates to clinical medical imaging, and more particularly, to a method and a system for medical imaging and information display.

BACKGROUND OF THE INVENTION

Nowadays, clinical medical imaging plays an important role to provide doctors with the necessary information about patients. For example, a variety of imaging modalities, such as CT, MRI, Ultrasound or the like, are currently available to assist doctors in this regard. For each imaging modality, there are different imaging modes.

Taking Ultrasound as an example, ultrasound imaging has been widely applied in clinical applications due to it being a non-radiation, non-invasive, real-time and low-cost technique. As is well known in the art, there are different kinds of modes in ultrasound imaging, for example but not limited to, B-mode ultrasound, Color ultrasound, Contrast ultrasound, Elastography ultrasound including Strain ultrasound and Quantitative Elastography ultrasound.

In order to have comprehensive information about patients, doctors often need to combine imaging data from different imaging modes. How to optimally use all the imaging data is a difficult problem for human beings. The main reason is that the clinical object exists in a high dimensional space and human perception is limited and lacks the competence to solve the high-dimensional problem.

Computerized techniques such as machine learning are better capable to handle the high dimensional problem than human beings. Therefore, a clinical decision support (CDS) system based on computerized techniques plays an important role in providing such comprehensive information for doctors.

However, for a clinical object, doctors are required to first select the region of interest (ROI) for denoting the object in an imaging plane or imaging volume of a patient and then apply the related analysis or computerized algorithms to provide the structural information, functional information or even the diagnostic information themselves.

U.S. Pat. No. 6,186,949 B1 discloses method and apparatus for three-dimensional flow imaging using coded excitation. In performing three-dimensional flow imaging using coded excitation and wall filtering, a coded sequence of broadband pulses (centered at a fundamental frequency) is transmitted multiple times to a particular transmit focal position. On receive, the receive signals acquired for each firing are compressed and bandpass filtered to isolate a compressed pulse centered at the fundamental frequency. The compressed and isolated signals are then wall filtered to extract the flow imaging data. This process is repeated for a multiplicity of transmit focal positions in each of a multiplicity of scanning planes to acquire a volume of flow imaging data. Volume rendered images are then produced which allow the user to view the data volume from any angle. In addition, the data volume may be reformatted to produce two-dimensional images of arbitrary cut planes through the data volume.

SUMMARY OF THE INVENTION

The inventors of the present invention have recognized that the CDS system based on manual selection of ROI as described above has a number of drawbacks.

Firstly, the ROI selection process is performed with different modes individually and doctors need to select the ROI for different modes to try to denote the same object. It cannot be performed real-time and it is not possible to provide CDS information in the course of the screening process. Moreover, this selection process may lead to mistakes and is time-consuming. Sometimes doctors, especially junior doctors, experience difficulties in selecting the right ROI and therefore overlook the object to be examined or diagnosed. Additionally, the CDS information is provided per ROI, e.g. one value for the whole ROI. In other words, the granularity of the CDS information is low. In addition, as doctors are provided with the information from different modes for one local ROI, it is difficult for them to obtain an overall understanding of the clinical object.

Secondly, image data from different imaging modes are generally obtained sequentially by switching among different modes, and the radio frequency signal transmitted is generally different for different imaging modes. When the transmitted radio frequency signal is different, the number and position of the pixels in the obtained image are different as well. Additionally, the imaging plane or imaging volume in different modes can be different due to the change in the relative position between the imaging apparatus and the patient. For example, during ultrasound screening, the position and/or angle of the ultrasound probe held by the doctor can be changed so that the field of view of the ultrasound probe is changed as well when the doctor switches between different modes. Therefore, the image data of different imaging modes do not have pixel-level correspondence. As a result, the pixel-level combination of image data of different modes becomes very complex.

As a special case, for certain imaging modes, the simultaneous imaging of different modes with pixel-level correspondence can be considered to be realized. For example, the radio frequency (RF) signal sequence used for Color mode is the same as that used for the B-mode imaging mode. Based on this, pixel-level correspondence between Color and B-mode is achieved and the pixel-level combination of the image data from these two modes can be realized. However, nowadays the combination of these two modes is nothing but pixel-wise superposition of the imaging data. That is, the combined imaging data for each pixel is a sum of the imaging data of that pixel in the two modes. Thus, the combined imaging data do not provide any additional CDS information. The doctors have to use them as conventional imaging modes and process them in the conventional way. Therefore, how to simultaneously process the high dimensional data in a satisfactory manner still remains a difficult challenge for doctors. Meanwhile, the RF signals of these kinds of current imaging modes are often too limited to generate different imaging modes. The number generally does not exceed two, which may be insufficient for providing enough imaging information and realizing the subsequent CDS processing step.

Therefore, it would be advantageous to provide a novel method and system for medical imaging and information display in order to provide doctors with comprehensive information from different imaging modes without the doctors being burdened with selecting the ROI from imaging data of different modes. The different imaging modes are not limited to specific modes and the number may be as large as possible, if desired, in comparison with the above-mentioned prior art.

In accordance with an aspect of the present invention, there is proposed a method of medical imaging and information display, comprising: acquiring imaging data of each point of a plurality points in an imaging plane or imaging volume of a subject in each mode of a plurality of different imaging modes of a medical imaging apparatus; deriving, for said each point, a value by applying the imaging data of the point in said each mode and the imaging data of at least one other point of said plurality of points adjacent to the point in said each mode to a predetermined model, wherein the predetermined model is selected in accordance with a clinical medical application related to the subject; constructing an image based on all the derived values; and displaying the constructed image to a user.

Compared to the conventional image processing method, the method according to the present invention does not require doctors to select the region of interest (ROI) for denoting the object in different modes and then apply the related analysis or computerized algorithms to provide the information themselves, so that the method according to the invention greatly reduces the burden of doctors.

Furthermore, since in the method according to the present invention, a value is derived for each point in the imaging plane or imaging volume by applying the imaging data of the point and the imaging data of at least one other point adjacent to the point to a predetermined medical application related model, and then an image is constructed based on all the derived values and displayed to a user, the method enables real-time screening for doctors. For example, during ultrasound screening, when the doctor moves the probe to a particular place, the derived values for each pixel in the field of view are vividly displayed as an image and presented to the doctor in real-time, and when the doctor changes the angle or position of the probe, the presented image is updated accordingly. Moreover, it can present image carrying information about the clinical object directly on pixel level, so that doctors can be provided with a higher-definition image as compared to the conventional ROI method and obtain an overall understanding of the clinical object. Thus, the doctor will not overlook the object.

Meanwhile, the value for each point in the imaging plane or imaging volume is not derived only from the imaging data of the point per se, but also based on the imaging data of at least one other point adjacent to the point. In this way, using the method may further improve the quality of the derived value and/or allow the derived value to deliver more clinical information, resulting in a better and more informational, constructed image. In other words, the output image is more useful and reliable for doctors.

Here, those skilled in the art may easily understand that the distance between each of the at least one other point and the point does not exceed a predetermined value. For example, in an example, the at least one other point may be points closest to the target point. In other words, they may be upper right, upper left, lower right, lower left points with respect to the target point in the imaging plane or imaging volume.

The predetermined model can be any model related to a clinical medical application to deliver clinical information related to the clinical medical application.

Typically, the predetermined model is non-linear. In one example, the predetermined model is a machine learning based model. In another example, the predetermined model may be a clinical decision support (CDS) model, so that the constructed image may provide doctors with the clinical decision support information. As for the CDS model, it will be understood by those skilled in the art that the CDS model may be a model which outputs diagnosis information with respect to a subject such as a patient. However, the CDS model is not limited thereto, some kinds of CDS model are such that the doctor is not able to obtain the diagnostic result or health condition of the subject based on the derived values or the constructed image. In other words, the output value of the CDS model may be structural or functional information regarding the subject, and doctors cannot get the diagnostic result of the subject directly on the basis of the structural or functional information.

Conventionally, images of different modes may be illustrated in a single image by overlaying/superimposing them together. In case of overlaying multiple images, the image value of the multiple images are superimposed pixel-by-pixel, optionally with different weights. To the contrary, according to the embodiment of the present invention, the derived value for each point in the imaging plan or volume is not only dependent on the image data of the point itself but also dependent on the image data of the adjacenet points. Furthremore, the predermined model is selected in accordance with a clinicle medical appliaction, which is typically non-linear.

In one example, the step of constructing an image based on all the derived values may comprise constructing an image in such a way that each point in the image has a different brightness or color in accordance with the value of the corresponding point in the imaging plane.

In this way, doctors may be provided with a clearer display so that they can easily identify the portions that need further observation or evaluation.

Please note that the method according to the present invention may be applied to different imaging modalities, for example, CT, MRI, Ultrasound, or the like. In other words, the medical imaging apparatus used in the method of the present invention may be a CT imaging apparatus, an MR imaging apparatus, or an ultrasound imaging apparatus. Alternatively, the medical imaging apparatus may also be a combined modality imaging apparatus. For example, it may be a CT/MRI combined imaging apparatus which can perform the CT imaging modality and MRI modality in one apparatus.

In the case of an Ultrasound imaging apparatus, the transmitted signal sequence for the ultrasound imaging apparatus is designed in accordance with time sequence, signal energy, and beam forming pattern of the transmitted signal, so that the imaging data in the different imaging modes are acquired simultaneously and point-level correspondence of the imaging data is established among the different imaging modes.

In accordance with another aspect of the present invention, there is proposed a system for medical imaging and information display, comprising: a medical imaging apparatus for acquiring imaging data of each point of a plurality points in an imaging plane or imaging volume of a subject in each mode of a plurality of different imaging modes; a processing apparatus, comprising a deriving unit for deriving, for said each point, a value by applying the imaging data of the point in said each mode and the imaging data of at least one other point of said plurality of points adjacent to the point in each said mode to a predetermined model, wherein the predetermined model is selected in accordance with a clinical medical application related to the subject; and a constructing unit for constructing an image based on all the derived values. The system further comprises a display apparatus for displaying the constructed image to a user.

Various aspects and features of the disclosure are described in further detail below. These and other aspects of the invention will be apparent from and elucidated with reference to the embodiment(s) described hereinafter.

DESCRIPTION OF THE DRAWINGS

The present invention will be described and explained hereinafter in more detail in combination with embodiments and with reference to the drawings, wherein.

Figure 1:
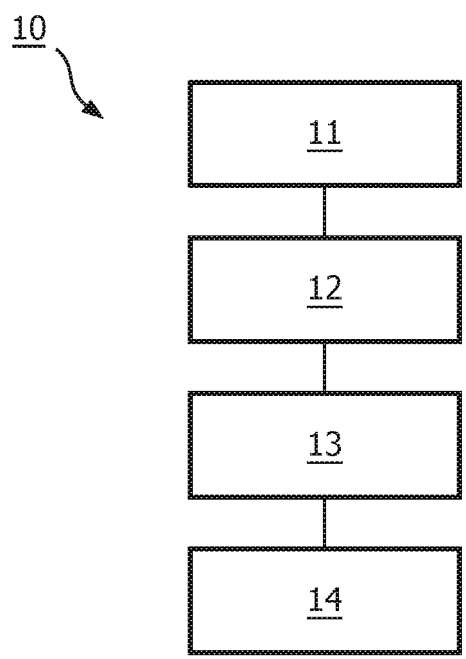
FIG. 1 is a flowchart of the method according to the present invention.

The same reference signs in the figures indicate similar or corresponding features and/or functionalities.

DETAILED DESCRIPTION OF THE EMBODIMENTS

The present invention will be described with respect to particular embodiments and with reference to certain drawings, but the invention is not limited thereto but only by the claims. The drawings described are only schematic and are non-limiting. In the drawings, the size of some of the elements may be exaggerated and not drawn to scale for illustrative purposes.

FIG. 1 is a flowchart of the method 10 of medical imaging and information display in accordance with an embodiment of the present invention.

In the following, details of the method 10 will be described, especially in conjunction with FIG. 2, which is a block diagram of the system 20 for implementing the method 10 shown in FIG. 1.

Figure 2:
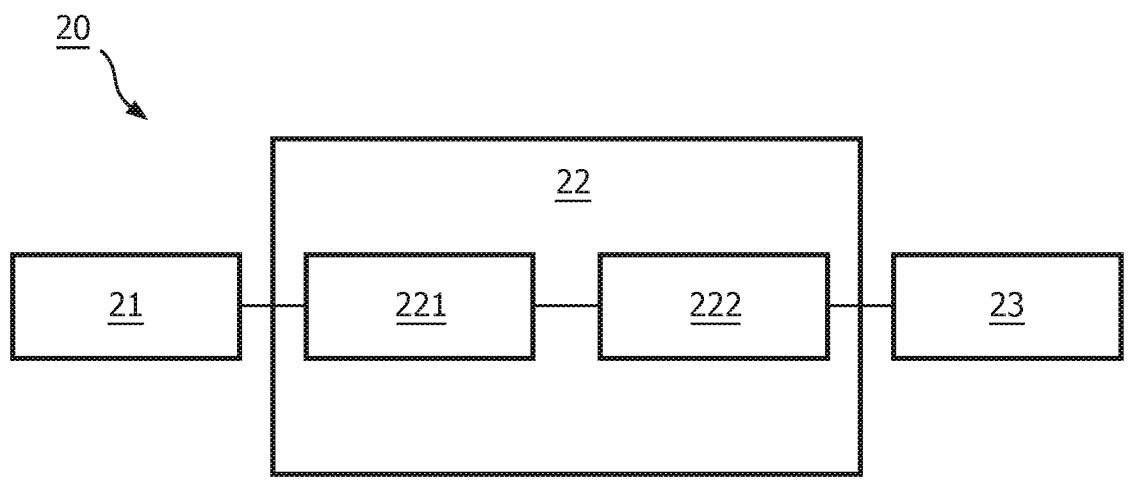
FIG. 2 is a block diagram of the system according to the present invention.

As can be seen from FIG. 2, the system 20 for medical imaging and information display in accordance with an embodiment of the present invention comprises a medical imaging apparatus 21, a processing apparatus 22 and a display apparatus 23.

Here, the medical imaging apparatus 21 may be a CT imaging apparatus, an MR imaging apparatus, an Ultrasound imaging apparatus. Alternatively, the medical imaging apparatus 21 may also be a combined modality imaging apparatus. For example, it may be a CT/MRI combined imaging apparatus which can perform the CT imaging modality and MRI modality in one apparatus. In the following, an Ultrasound imaging apparatus is used as an example of the apparatus 21.

Further, the processing apparatus 22 is coupled with the medical imaging apparatus 21 and may be a computer or other apparatus with CPU or microcontroller. In the processing apparatus 22, there are at least a deriving unit 221 and a constructing unit 222 for processing the imaging data from the imaging apparatus 21. Please note that it will be easily understood by those skilled in the art that, although the deriving unit 221 and the constructing unit 222 are shown as separate units in the processing apparatus 22, they may be implemented in one and the same unit as well. For example, the two units can be a CPU in a computer.

The display apparatus 23 may be any conventional display apparatus, for example, the display of a computer or an individual display screen in a console.

At the beginning, the medical imaging apparatus 21 acquires imaging data of a subject such as a patient as information in different imaging modes. As mentioned above, in the case that the imaging apparatus 21 is an Ultrasound imaging apparatus, it acquires the imaging data of each point in an imaging plane or imaging volume of the subject in a plurality of different imaging modes (step 11 in FIG. 1). The plurality of different ultrasound imaging modes comprise, but are not limited to, B-mode, Color, Contrast, Elastography ultrasound including Strain ultrasound and Quantitative Elastography ultrasound.

Next, the deriving unit 221, which is coupled with the medical imaging apparatus 21, derives, for said each point, a value by applying the imaging data of the point and the imaging data of at least one other point of said plurality of points adjacent to the point to a predetermined model (step 12 in FIG. 1).

Further, the constructing unit 222 would then construct an image based on all the derived values (step 13 in FIG. 1).

Here, the predetermined model is selected in accordance with a clinical medical application related to the subject.

In one example, the predertermined model may be a machine learning based model.

In one example, the predetermined model may be a clinical decision support (CDS) model, so that the constructed image may provide doctors with the clinical decision support information.

As can be understood by those skilled in the art, the CDS model may be a model which outputs diagnosis information for the subbject. It may be a CDS model that is pre-established or pre-trained for the clinical object or may also be an existing CDS model that is suitable for the clinical medical application related to the subject.

In one example, the CDS model may be a model used for liver diagnosis. Specifically, when a doctor diagnoses a subject with a liver disease, based on the information from ultrasound B-mode imaging, Color and Elastography, using the method of the present invention, the doctor is directly provided with an image (or an image sequence) of different intensities at different locations which denote the probabilities of a liver disease for the subject.

For another example, the CDS model may provide the output result regarding the blood supply function of the subject. When a doctor evaluates the blood supply function in an organ of a subject, based on the information of different ultrasound modes such as B-mode, Color and Contrast imaging, by simultaneously using the imaging data from the three modes, the CDS model can directly display the score values on the image at every location denoting the blood supply function at that location in the organ. With the method of the present invention, the object of a clinical application is directly provided with the associated "image" for doctors, which could support doctors to locate the ROI for a possible disease and also be able to get the optimal clinical decision support from the whole displayed image.

However, the CDS model is not limited thereto. As is well known in the art, some kinds of CDS model are such that the doctor is not able to obtain the diagnostic result or health condition of the subject on the basis of the derived values or the constructed image. In other words, the output value of the CDS model may be structural or functional information regarding the subject. Although doctors cannot get the diagnostic result of the subject directly on the basis of such structural or functional information, this structural or functional information can be helpful in assisting doctors and facilitates making the diagnosis.

In one example, the CDS model may be used to obtain a clearer anatomical structure by utilizing the imaging data from the B-mode, Color mode, and Elastography mode. For the anatomical structure, it may appear as a high intensity of the B-mode echo signal. Although the term "high intensity" used here may also correspond to other things, in this case it only represents the high echo energy. The Color mode may provide blood information to some extent, and often there is no structure inside the strong signals of the ultrasound color image. The Elastography mode provides elasticity information which may represent the structure from another point of view to some extent. With these three kinds of information for imaging the anatomical structure, an artificial model should be established to simultaneously "utilize" them, and the output image directly denotes the structure distribution of interest.

In a further example, the CDS model may be used to obtain the vessel distribution by utilizing the imaging data from the B-mode and Contrast mode. Inside a vessel, there is blood. Also the vessel has its own structure which might be represented as a high intensity of the B-mode echo signal. By considering these two aspects simultaneously, the vessel may be better defined than by only considering one of them. Therefore, with the two kinds of information, an artificial model could be trained to denote the probability of a position being a vessel. Then the output image denotes the vessel distribution.

In still another example, the CDS model may be used to obtain the tissue (material) image by utilizing the imaging data from the B-mode, Color mode, Contrast mode and Elastography mode. Some tissues have many characteristics, and B-mode, color, contrast and elastography, etc. may represent one or some of these characteristics. By considering all of them, the kind of tissue might be well defined. To consider them all, an artificial model should be established. Then the output image may denote different tissue distributions according to different applications.

Here, please note that, in step 12, the value for each point in the imaging plane or imaging volume is not derived only from the imaging data of the point per se, but also based on the imaging data of at least one other point adjacent to the point. In this way, further improvement of the quality of the derived value and thus the constructed image may be achieved.

Those skilled in the art may easily understand that the distance between each of the at least one other point and the point does not exceed a predetermined value. For example, in an example, the at least one other point may be points closest to the target point. In other words, they may be the upper right, upper left, lower right, lower left points with respect to the target point in the imaging plane or imaging volume.

Next, the display apparatus 23 outputs the constructed image to the user (step 14 in FIG. 1).

In comparison with the conventional image processing method, the method 10 according to the present invention does not require doctors to select the region of interest (ROI) for denoting the object in different modes and then apply the related analysis or computerized algorithms to provide the information themselves, thereby greatly reducing the burden of doctors.

Furthermore, since in the method according to the present invention each point in the imaging plane or imaging volume has a value, which is output from the predetermined medical application-related model in accordance with the imaging data of the point and the imaging data of at least one other point adjacent to the point, and then an image is constructed based on all the derived values of all the points and displayed to a user, the method enables real-time screening for doctors.

For example, during ultrasound screening, when the doctor moves the probe to a particular place, the derived values for each pixel in the field of view are vividly displayed as an image presented to the doctor in real-time, and when the doctor changes an angle or position of the probe, the presented image is updated accordingly.

Moreover, the method of the present invention can present image carrying information about the clinical object directly on pixel level, so that doctors may be provided with an image with higher definition as compared to the conventional ROI method and thus do not overlook the object.

Further, in the method according to the present invention, the value for each point in the imaging plane or imaging volume is not derived only from the imaging data of the point per se, but also based on the imaging data of at least one other point adjacent to the point. In this way, a further improvement of the quality of the derived value and thus of the constructed image may be achieved.

In one example, step 13 of constructing an image based on all the derived values may comprise constructing an image in such a way that each point in the image has a different brightness or color in accordance with the value of the corresponding point in the imaging plane.

For example, if the value of a point in the imaging plane is higher, the brightness for the corresponding point in the obtained image is higher. Alternatively, if the value of a point in the image plane is higher, the brightness for the corresponding point in the obtained image is lower.

In this way, doctors may be provided with a clearer display, so that they can easily identify the portions that need further observation or evaluation.

The principle of the present invention and the basic flow chart of the method according to the invention have been discussed in detail hereinabove. Next, step 11 will be explained in detail to clarify its requirement.

As mentioned above, in step 11, the imaging data of each point in an imaging plane or imaging volume of a subject in a plurality of different imaging modes should be acquired (step 11 in FIG. 1).

The reason for using the expression "the imaging data of each point in different imaging modes" is that, in order to perform pixel-level image processing, pixel-level correspondences among all the modes should be obtained to guarantee information correspondence at every location (point) for the following process. For CT and MR imaging, due to the imaging principle thereof, pixel-level correspondences among all the modes seem to be feasible. For ultrasound imaging, however, it is very difficult.

Specifically, currently, the ultrasound system cannot directly provide pixel-level correspondences upon scanning mode changes. For different modes (B-mode, Color, Contrast, Strain, and Quantitative Elastography), the images are quite different. Therefore the conventional registration algorithms are no longer suitable here.

As mentioned in the background of the present invention, for some ultrasound imaging modes, simultaneously imaging different modalities with pixel-level correspondences can be considered to be realized. For example, as the color imaging, the radio frequency (RF) signal sequence for color modality can be also used to get the B-mode imaging modality. Based on this, the pixel-level correspondence between color and B-mode is realized for real-time imaging. However, for using these simultaneous modalities, nowadays they are simply pixel-level combined for the display, and then doctors need to use them as the conventional imaging modalities and process them in the conventional ways. Therefore, how to simultaneously process the high dimensional data well still is a difficult challenge for doctors. Meanwhile, the RF signals of these kinds of current imaging modalities are often too limited to generate different imaging modes. The number of said signals is generally just two, which may be insufficient for providing enough imaging information and realizing the subsequent CDS processing. When considering a large range of imaging modes in ultrasound, their raw imaging RF data are quite different.

Therefore, in view of the above mentioned problem regarding ultrasound imaging, the inventors of the present invention further propose to specifically design the transmitted signal sequence for the ultrasound imaging apparatus in order to achieve pixel-level correspondence among all the ultrasound imaging modes.

In principle, the inventors of the present invention have found that the transmitted signal sequence for the ultrasound imaging apparatus may be designed in accordance with time sequence, signal energy, and beam forming pattern of the transmitted signal, so that the imaging data in the different imaging modes are acquired simultaneously and point-level correspondence of the imaging data is established among the different imaging modes.

In one example, the imaging modes comprise at least two of the five modes: B-mode, Color, Contrast, Strain, and Elastography.

In a further example, if all five ultrasound imaging modes are to be used, the transmitted signal sequence may be designed to comprise three typical ultrasound plane-transmits interpolated with two high-energy and high-focused ultrasound plane-transmits, in which the phase of the second typical ultrasound plane-transmit is inversed.

Generally, a transmit signal sequence for imaging in one mode can be considered to consist of many ultrasound transmits. For different modes, the required combinations of transmits are different. For example, B-mode imaging requires at least one typical ultrasound plane-transmit. Color imaging should require at least three typical ultrasound plane-transmits. Strain imaging requires at least two typical ultrasound plane-transmits. Shear wave quantitative Elastography requires at least two high-energy and high-focused ultrasound plane-transmits. Contrast imaging requires at least two typical ultrasound plane-transmits and one inverse plane-transmit. For the method of the present invention, the simultaneous imaging of different modes is required. If the conventional transmitting hardware does not change and all the transmitted signals of the abovementioned modes are just directly combined so as to form a cascade of the different transmit signal sequences, there will be at least 1+3+2+2+3=11 plane-transmits for the total transmitted signal sequence. Transmit signal sequences consisting of too many plane-transmits may result in a low frame rate for imaging and may further affect the "simultaneous obtaining of the information of different modes".

Based on this consideration, the transmitted signal sequence and the related hardware should be specifically designed. The basic principle is that the plane-transmits for one mode should also be applicable for the imaging of other modes, for which the detailed order of appearance in one signal sequence may change. Also with respect to the above example, one possible RF signal transmitted sequence may be three typical ultrasound plane-transmits interpolated with two high-energy and high-focused ultrasound plane-transmits, in which the second typical ultrasound plane-transmit should be inverted in phase. For receiving, the first typical ultrasound plane-transmit is typically received to generate the B-mode imaging. The first and third typical ultrasound plane-transmits are typically received to generate the strain mode. The first and third typical ultrasound plane-transmits are typically received and the second typical ultrasound plane-transmit is inversely received to generate the Color mode. For the two high-energy and high-focused ultrasound plane-transmits, the fast receiving scans should be performed directly after each of them and then the shear wave Elastography can be obtained. For the Contrast mode, the three typical ultrasound plane-transmits are typically received to generate the contrast image information. It can be seen that the total number of the plane-transmits in the sequence is only 5.

Since all the different modes come from the same raw transmitted signal sequence, the pixel-level correspondences between different modes can be well obtained. Due to different hardware characteristics, the maximum endurable number of plane-transmits for real-time imaging may vary and therefore more plane-transmits may be used for one mode. But the basic design principle for the method of the present invention should remain the same.

Although FIG. 2 only shows the basic block diagram of the system 20 according to the present invention, it may be easily understood by those skilled in the art that, corresponding to each step in the above described method 10, there could be a corresponding unit to perform the relevant method step.

As for the units 221 and 222 comprised in the processing apparatus 22, in one example, the processing apparatus 22 per se may be a personal computer with CPU and memory, a Single-chip Microcomputer or a CPU (i.e., a processing unit) alone. Therefore, the respective units comprised therein may be implemented as software or computer-readable instructions.

However, as will be easily understood by those skilled in the art, the respective units, may be hardware entities as well. In other words, the processing apparatus 22 may be composed of distinct hardware modules. Each of the units may be implemented by a single processor or a plurality of processors.

Please note that the steps of the method 10 shown in the present invention should not be limited to the steps mentioned above. It will be apparent to those skilled in the art that the various aspects of the invention claimed may be practiced in other examples that depart from these specific details.

Further, please note that although ROI is used throughout the specification, those skilled in the art may easily understand that the term ROI "region of interest" is used in the case of a 2D scenario, whereas the term VOI, i.e., "volume of interest", is used in the case of 3D.

Furthermore, as can be easily understood by those skilled in the art, in the apparatus claim enumerating several means, several of these means can be embodied by one and the same item of hardware. The mere fact that certain measures are recited in mutually different dependent claims does not indicate that a combination of these measures cannot be used to advantage.

It should be noted that the above-mentioned embodiments illustrate rather than limit the invention and that those skilled in the art would be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. In the system claims enumerating several units, several of these units can be embodied by one and the same item of software and/or hardware. The usage of the words first, second and third, et cetera, does not indicate any ordering. These words are to be interpreted as names.

The invention claimed is:

1. A system for medical imaging and information display, comprising:
   at least one processor in communication with an ultrasound probe; the processor further configured to:
   derive a imaging sequence corresponding to a plurality of planes within an imaging volume, where at least one of the plurality of planes corresponds to two or more imaging modes;
   receive imaging data acquired by the ultrasound probe in accordance with the imaging sequence;
   derive values for a plurality of points within each acquired plane, wherein a value for each particular point corresponds to:
      a locale of the particular point in each plane; and
      a clinical indication associated with other points adjacent to the particular point; and
   construct an image based on all the derived values.

2. The system according to claim 1, wherein a distance between the particular point and the adjacent point does not exceed a predetermined distance.

3. The system according to claim 1, wherein the system further comprises a display, and the processor is configured to display the constructed image on the display.

4. The system according to claim 2, wherein
   the imaging sequence comprises the time sequence, signal energy, and beam forming pattern of ultrasound signals tranmitted form the ultrasound probe.

5. The system of claim 1, wherein the imaging modes comprise at least two modes selected from the group consisting of B-mode, color mode, contrast mode, and elastography mode.

6. The system according to claim 1, wherein the derived value of the point corresponds to a brightless or intensity of the point within the imaging data.

* * * * *